United States Patent
Fukushima et al.

(10) Patent No.: US 6,482,988 B2
(45) Date of Patent: Nov. 19, 2002

(54) SULFUR COMPOUND CONTAINING TERPHENYL SKELETON

(75) Inventors: Hitoshi Fukushima, Tsukuba (JP); Takashi Tamaki, Tsukuba (JP)

(73) Assignees: Seiko Epson Corporation, Tokyo (JP); National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 09/790,624

(22) Filed: Feb. 23, 2001

(65) Prior Publication Data

US 2001/0044552 A1 Nov. 22, 2001

(30) Foreign Application Priority Data

Feb. 23, 2000 (JP) ........................................ 2000-046440
Feb. 19, 2001 (JP) ........................................ 2001-041833

(51) Int. Cl.$^7$ ........................................... C07C 321/28
(52) U.S. Cl. ............................. 568/22; 568/24; 568/25; 568/39; 568/51; 568/52
(58) Field of Search ............................. 568/52, 21, 22, 568/24, 25, 38, 39, 51

(56) References Cited

U.S. PATENT DOCUMENTS 5,347,015 A * 9/1994 Keller et al. ................. 548/455
5,514,501 A * 5/1996 Tarlov ............................ 430/5

FOREIGN PATENT DOCUMENTS

JP         9-255621 A      9/1997

OTHER PUBLICATIONS

CA:130:57611 ab of J Am. Chem. Soc. by Himmel et al f120(46) pp. 12069–12074 1998.*
Langmuir by Stadler et al vol. 17 pp. 2408–2415 2001.*
CA:119:257126 abs of Langmuir by Sabatani et al 9(11) pp. 2971–81 1993.*

"Physical Review E", vol. 59, No. 3, pp. 3033–3039, Mar. 1999, "Anchoring and orientational wetting of nematic liquid crystals on self–assembled monolayer substrates: An evanescent wave ellipsometric study".
Anchoring of Nematic Liquid Crystals on Self–Assembled Monolayers Formed from Alkanethiols on Semitransparent Films of Gold, J. Phys. Chem. 1995, vol. 99, pp. 16511–16515.
Surface Plasmon Resonance Imaging of Liquid Crystal Achoring on Patterned Self–Assembled Monolayers, J. Phys. Chem. B 1997, vol. 101, pp. 2143–2148.
Uniform Anchoring of Nematic Liquid Crystals on Self–Assembled Monolayers Formed from Alkanethiols on Obliquely Deposited Films of Gold, Langmuir 1996, vol. 12 pp. 2587–2693.
Mesoporus Platinum Films for Lyotropic Liquid Crystalline Phases, "Science", vol. 278, Oct. 31, 1997, pp. 838–840.
Optical Amplification of Ligand–Receptor Binding Using Liquid Crystals, "Science", vol. 279, Mar. 27, 1998, pp. 2077–2078.

* cited by examiner

Primary Examiner—Jean F. Vollano
(74) Attorney, Agent, or Firm—Oliff & Berridge, PLC

(57) ABSTRACT

A liquid crystalline sulfur compound exhibiting high anisotropic factor of dipolemoment is provided. A terphenyl skeleton sulfur compound expressed by the general formula (I) is provided. A compound is preferred wherein, in the general formula (I), m is 1, n is 5 to 18, and $R_3$ is an alkyl group wherein the number of carbon atoms is n or fewer than n. A method of synthesisng the terphenyl skeleton sulfur compound wherein, after implementing the synthesizing processes for a methoxy terphenyl derivative, a hydroxy terphenyl derivative, and terphenyl alkyloxy bromide derivative, that bromide derivative and thiourea are caused to react, etc. A self-assembled monolayer made using the terphenyl skeleton sulfur compound noted above is also provided.

9 Claims, 11 Drawing Sheets

(3 of 11 Drawing Sheet(s) Filed in Color)

SULFUR COMPOUND CONTAINING TERPHENYL SKELETON

BACKGROUND OF THE INVENTION

1. Field of the Invention

This invention relates to a new sulfur compound that contains a terphenyl skeleton. More particularly, the present invention relates to a sulfur compound that contains a liquid crystal terphenyl skeleton exhibiting high anisotropic factor of dipolemoment, which is useful as a novel functional thin film, with which the surface properties of the entire surface of the film can be reversibly controlled by applying an external stimulus such as an electric field, and dynamically changing the molecules and molecular aggregates that configure the self-assembled monolayer. The present invention further relates to a synthesisng method of such compound and to a self-assembled monolayer in which that compound is used, that contains a liquid crystal terphenyl skeleton exhibiting high anisotropic factor of dipolemoment, wherewith the surface properties of the entire surface of the film can be reversibly controlled by applying an external stimulus such as an electric field, and dynamically changing the molecules and molecular aggregates that configure the self-assembled monolayer.

2. Description of the Related Art

Conventionally, self-assembled monolayers (hereinafter called SAMs) that are formed when molecules spontaneously aggregate and are ordered merely by immersing a substrate of metal or the like in a solution of the target molecules have been developed in a wide range of fields. The most widely researched SAMs are organic sulfur SAMs such as alkane thiol SAMs and organic silane SAMs wherein a silane coupling agent is used. In particular, alkane thiols are chemical substances that spontaneously fabricate a SAM when a gold substrate (Au substrate) is immersed in an ethanol solution thereof. Systems resulting from combinations of metal films and thiol molecules play the central role in SAM research because of their stable chemical adsorbing properties and ability to form closely packed monomolecular film arrays.

Thiol derivatives having terphenyl skeletons used in SAMs are proposed, for example, in Sabatani, E., et al., Langmuir (1993), 9, 2974–2901, Himmel, H. J., et al., J. Am. Chem. Soc. (1998) 120, 12069–12074, and Ishida, T., et al., J. Phys. Chem. B. (1999) 103, 1686–1690.

With these thiol compounds, however, the packing of the molecular film readily takes on a herringbone structure due to the van der Waals intermolecular interaction between terphenyl moieties. When that happens, the molecular packing becomes stronger, and the 2-D (two dimensional) crystal structure of monolayer film on substrate also becomes stronger. This strong crystallinity becomes a large hindering factor in causing SAMs to move under the appropriate strength of an electric field using the high anisotropic factor of dipolemoment of the molecules. Thus there has been a need to develop compounds capable of forming SAMs that exhibit no crystallinity, and particularly SAMs that exhibit no crystallinity and at the same time exhibit liquid crystal properties (being fluid and exhibiting flexibility), while maintaining the high-degree of anisotropic factor of the dipolemoment.

Now, in Japanese Patent Application Laid-Open No. H9-255621/1997, certain compounds having a terphenyl skeleton are proposed as macromolecular dispersion type liquid crystal materials that exhibit high anisotropic factor of dipolemoment and that can be used in liquid crystal display elements. However, no example of the synthesis of a liquid crystal sulfur compound exhibiting high anisotropic factor of dipolemoment whereas maintaining the high-degree of chemical affinity to metal surfaces such as gold has been reported to date.

SUMMARY OF THE INVENTION

Accordingly, an object of the present invention is to provide a liquid crystal sulfur compound exhibiting high anisotropic factor of dipolemoment with strong affinity to metal surfaces.

As a result of various studies, the inventors discovered that sulfur compounds containing a terphenyl skeleton having a certain structure can achieve the object stated above, and thus arrived at the present invention.

Specifically, the present invention provides sulfur compounds containing the terphenyl skeleton represented by the general structural formula (I) given below.

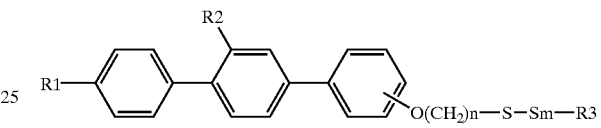

(I)

(where R1 is a nitrile group, halogen atom, hydrogen atom, methyl group, or trifluoromethyl group, R2 is a halogen atom, nitrile group, or trifluoromethyl group, R3 is

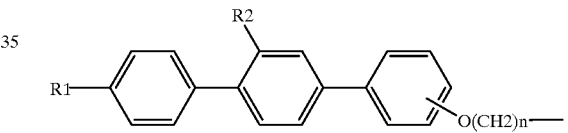

(A)

or an alkyl group having 1 to 20 carbon atoms, n is a number from 1 to 20, and m is 0 or 1.

BRIEF DESCRIPTION OF THE DRAWINGS

The file of this patent contains at least one drawing executed in color.

DESCRIPTION OF THE PREFERRED EMBODIMENTS

Figure 1:
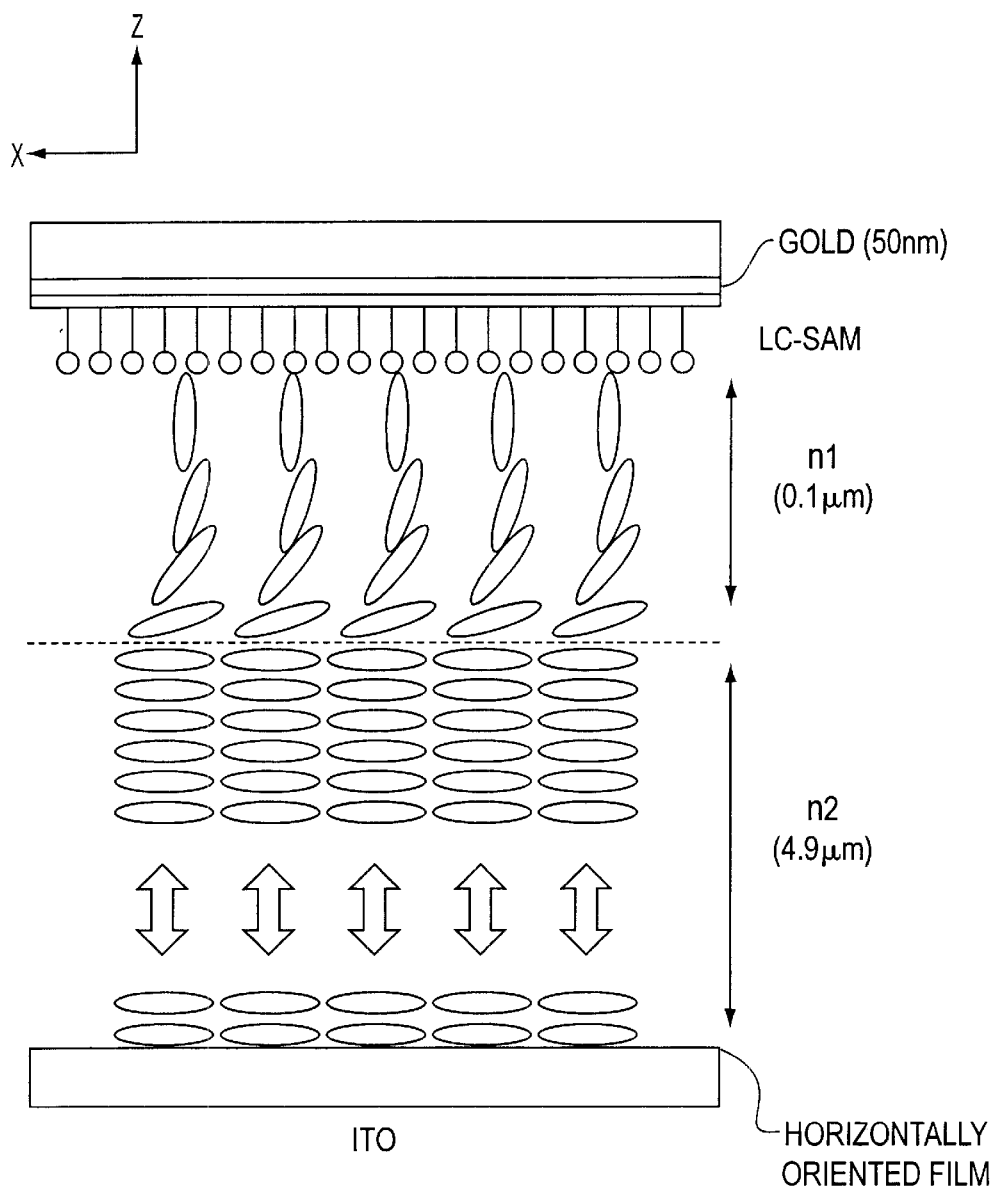
FIG. 1 is a model diagram representing the condition of a liquid crystal cell containing a SAM formed from a terphenyl skeleton sulfur compound relating to the present invention when an electric field is applied.

A detailed description is now given of the sulfur compound containing a terphenyl skeleton hereinafter called "terphenyl skeleton sulfur compound" that is the compound of the present invention.

The terphenyl skeleton sulfur compound of the present invention is a new sulfide compound or disulfide compound expressed by the general structural formula (I) given above. That is, the terphenyl skeleton sulfur compound of the present invention is a compound having a structure wherein the two groups positioned on both ends of one or two sulfur atoms is asymmetrical. By "asymmetrical" here is meant a relationship wherein, when the SAM is formed, a free space can be made by the two groups noted above, and molecular motion can be induced smoothly toward that free space.

With the terphenyl skeleton sulfur compound of the present invention, because it has the asymmetrical structure described above, SAMs formed thereby do not become high-density two-dimensional mono-molecular crystals, but the molecules are given freedom and free space is created so as to ease the molecular motion in SAMs induced by electric field. For that reason, the SAM becomes amorphous, and, when an electric field is applied from the outside, the monomolecular aggregates in SAMs exhibiting anisotropic factor of dipolemoment move in the direction of the electric field vector. Thereupon, a benefit is obtained in that molecular motion is induced smoothly by the existence of the free space.

In conventional terphenyl-based SAMs, crystallinity is very strong. Therefore the molecular film is stable and it is difficult to induce conformational changes in SAMs over time therein with an external force. The compound of the present invention eliminates the source of streric hindrance along the lateral direction in SAMs, In the general formula (I) given above, the halogen atoms represented by $R_1$ and $R_2$ may be fluorine atoms, chlorine atoms, bromine atoms, or iodine atoms, of which the fluorine atom is preferable, Of alkyl groups having 1 to 20 carbon atoms, represented by $R_3$, alkyl groups having 5 to 18 carbon atoms are preferable, and those having 8 to 14 carbon atoms being even more preferable. Also, it is preferable that the number of carbon atoms in the alkyl group be either the same as or smaller than the number n. The number n is a number from 1 to 20 that is the same as the number of carbons in the alkylene group ether-bonded with the terphenyl skeleton, preferably being a number from 5 to 18, but more preferably from 8 to 14, and most preferably 12.

There is no limitation on the location on the benzene ring used for the substitution of the —O(CH$_2$)$_n$—S—S—R$_3$ group, and either of an ortho-, meta-, or para-configuration is permissible.

Examples of the terphenyl skeleton sulfur compounds of the present invention include, for example, compounds wherein, in the general formula (I) above, m is 0, n is 1 to 20, and $R_3$ is the group (A) noted above, compounds wherein, in the general formula (1), m is 1, a is 1 to 20, and $R_3$ is the group (A), and compounds wherein, in the general formula (I), m is 1, n is 1 to 20, and $R_3$ is an alkyl group wherein the number of carbon atoms is either n or fewer than n. Compounds wherein, in the general formula (I), n is 5 to 18 are preferable, with those wherein n is 8 to 14 being particularly preferable Specific preferred examples of such terphenyl skeleton sulfur compounds include the compounds LC-(1) to LC-(3) given below.

LC-(1)

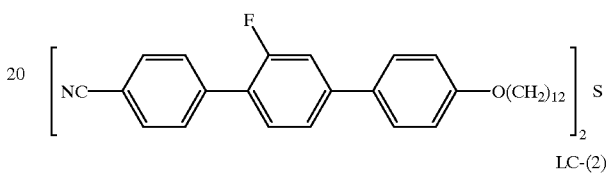

LC-(2)

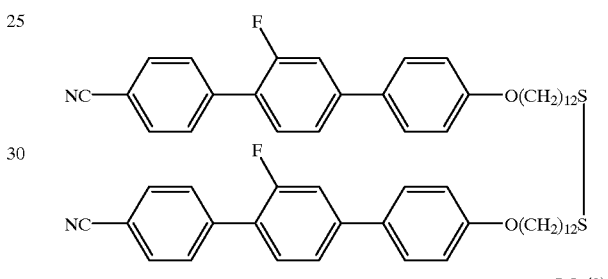

LC-(3)

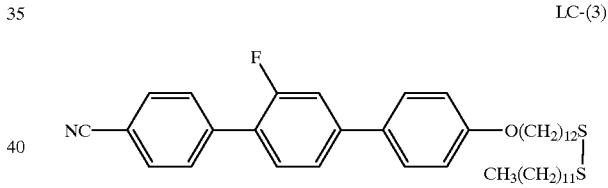

Among these compounds, those wherein, in general formula (I), m is 1, n is 5 to 18 but preferably 8 to 14, and $R_3$ is an alkyl group wherein the number of carbon atoms is n or fewer than n (especially chemical LC-(3)) are useful, and to be preferred for the following reason. That is, the compounds noted above are such that, when they are formed into a SAM, a degree of freedom that is just the area of the alkyl chain cross-section (approximately 20 square Ångstroms) appears in the space between adjacent terphenyls. When an electric field is applied to this SAM from the outside, the molecular portions (terphenyl portions) exhibiting large anisotropic factor of dipolemoment move in the direction of the electric field vector. This enhances further the effect of inducing molecular motion.

The terphenyl skeleton sulfur compound of the present invention, as described earlier, exhibits anisotropic factor of dipolemoment and liquid crystal properties, and can be used, for example, as the molecular material, which induces dynamic response of SAMs on gold substrates. Here, in order to verity the electric field movement functions such as responsiveness to an electric field in the SAM, an atomic force microscope (AFM) can be used. Specifically, the functions noted above can be verified by the molecular condition according to the AFM images of the SAM before and after applying the electric field from the outside. That is, if the molecules forming the SAM are in a packing conditions then regular conditions will appear in the AFM images both before and after electric field application. If the structure is looser, with free space in the condition of the molecules forming the SAM, random conditions will appear in the AFM image prior to electric field application, and regular conditions will appear in the AFM image after electric field application. Thus, when the molecules forming a SAM are in a packing condition, the electric field movement function can be judged to be low, whereas, conversely, when the structure is loose, with free space in the condition of the molecules forming the SAM, the electric field movement function can be judged to be high.

The verification of the electric field movement functions in SAMs can also be done using a dynamic surface measurement apparatus (such as a surface plasmon resonator (SPR) or the like).

With the terphenyl skeleton sulfur compounds of the present invention, furthermore, such surface properties as wettability can be controlled, wherefore they can be used not only in electric field responsive SAMs but also in various other applications where these properties can be manifested.

Next, describing the method of synthesising the terphenyl skeleton sulfur compounds of the present invention, that synthesising method is a preferable method for synthesising the new terphenyl skeleton sulfur compound described earlier, which may be specifically represented as follows.

Next, to describe the self-assembled monolayer of the present invention, the self-assembled monolayer of the present invention is a new functional thin film that uses a liquid crystal terphenyl skeleton sulfur compound that exhibits high anisotropic factor of dipolemoment, as described earlier. Hence, by applying an external stimulus such as an electric field, monomolecular aggregates in SAM, which spontaneously immobilised on to metal surface by chemisorption, are to be ossilated dynamically. Through this dynamic change of monomolecular level in SAM, the physical properties of the entire surface of the film can be reversibly controlled.

EMBODIMENTS

The present invention will now be described in greater detail in terms of embodiments, but it should be understood that the present invention is in no way limited to or by these embodiments.

Embodiment 1

(Compound LC-(1) Synthesis)

In synthesizing the compound LC-(1), first, following the synthesis route indicated below, syntheses of the compound P-(1), the compound P-(2), and the compound LC—Br are conducted successively.

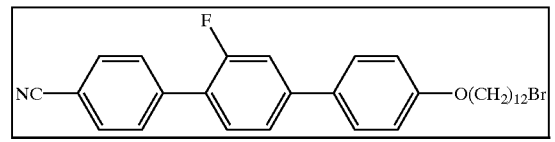

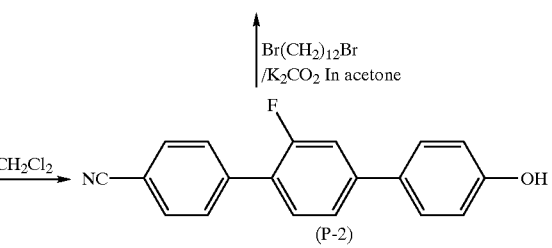

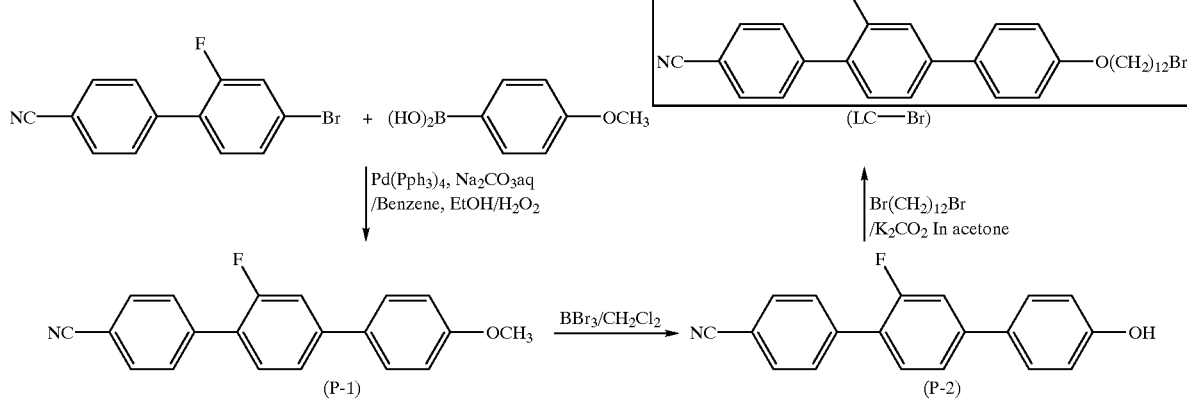

That is, a methoxy terphenyl derivative is obtained from a bromobiphenyl derivative and methoxybenzene boric acid. Then, from that and tribromo borane, a hydroxy terphenyl derivative is obtained. Then, from that and a dibromo alkane, a terphenyl alkyloxy bromide derivative is obtained. After that, the bromide derivative is made to react with thiourea or, alternatively, that bromide derivative, sodium thiosulfate pentahydrate, and an alkane thiol are made to react to yield the terphenyl skeleton sulfur compound. Here, by causing the terphenyl alkyloxy bromide derivative and thiourea to react, a compound can be synthesised wherein, in the general formula (I) given earlier, m is 0, n is 1 to 20, and $R_3$ is the group (A) noted earlier. By causing the terphenyl alkyloxy bromide derivative and sodium thiosulfate pentahydrate and alkane thiol to react, a compound can be synthesised wherein, in general formula (I), m is 1, n is 1 to 20, and $R_3$ is the group (A) noted earlier, or, alternatively, a compound wherein, in general formula (I), m is 1, n is 1 to 20, and $R_3$ is an alkyl group wherein the number of carbon atoms is n or fewer than n.

(1) Synthesis of Compound P-(1)

10.2 g of 2-fluoro-4-bromo-4'-cyano biphenyl and 63 ml of benzene were placed in a flask, stirred, and dissolved in a nitrogen atmosphere. Into this flask, 0.4 g of tetrakis (triphenyl phosfine) palladium (0) and 48 ml of a 2M aqueous solution of sodium carbonate were added and stirred at room temperature. After that, 5.6 g of p-methoxybenzene boronic acid dissolved in 45 ml of ethanol were added dropwise into the reaction mixture. After the addition was completed, stirring was continued for another half day with reflux. After cooling, 2 ml of a 30% water solution of hydrogen peroxide was added to the reaction mixture and stirred at room temperature, then extracted with chloroform. After drying with magnesium sulfate and distilling off the solvent, the crude residue was recrystalised by a mixed solvent of acetone and methanol. Then, after purifying under a chloroform solvent with silica gel, the precipitate was recrystalised by acetone to yield colorless acicular crystals (yield=7.5 g).

The results of analyzing the crystals obtained are indicated below.

¹H-NMR (CDCl₃); δ=3.87 (3H, t, Ar—O—CH,), 7.00 (2H, d, Ar—H), 7.38–7.58 (5H, m, Ar—H), 7.72 (4H, q, Ar—H), mp 112–115° C. (temperature at which losing the liquid crystallinity=255–258° C.)

(2) Synthesis of Compound P-(2)

2 g of 4-cyano-2'-fluoro-4"-methoxy terphenyl and 50 ml of dichloromethane were placed in a flask and dissolved. Then 16 ml of BBr₃ (1M, dichloromethane solution) were added dropwise in. After the addition was completed, the reaction mixture was stirred for 2 days longer at room temperature. Then the reaction mixture was poured into cold water and stirred well. The solid material was filtered out and dried. This yellow solid material was recrystallized in a mixed solvent of acetone and water to yield white crystals (yield =1.34 g).

The results of analyzing the crystals obtained are indicated below.

¹H-NMR (CDCl₃); δ=6.97 (2H, d, Ar—H), 7.49–7.67 (5H, m, Ar—H), 7.87 (4H, q, Ar—H), 8.66 (1H, s, Ar—OH), mp 224–225° C. (temperature at which losing the liquid crystallinity=282–284° C.)

(3) Synthesis of Compound LC—Br 4.26 g of 1,12-dibromododecane, 1.26 g of potassium carbonate, and 30 ml of acetone were placed in a flask, to which, under stirring, a solution wherein 1.5 g of 4-cyano-2'-fluoro-4"-methoxy terphonyl was dissolved in 40 ml of acetone was slowly added dropwise in. After the addition was complete, the reaction mixture was stirred for 2 days longer and reflux was implemented. After verifying by TLC that all of the starting material had reacted, the reaction mixture no crystallinity was added to cold water and stirred well. Precipitated solid material was separated by filtering, and washed thoroughly with water and ethanol (to remove the unreacted 1,12-dibromododecane). After drying, the solid material was purified using silica gel column chromatography (chloroform/hexane=4/1). The white crystals obtained were washed thoroughly again in ethanol, and then vacuum dried to yield the targeted compound (white crystals) (yield=2.06 g).

The results of analyzing the crystals obtained are indicated below.

¹H-NMR (CDCl₃); δ=1.2–1.4 (18H, m, —CH₂—), 1.84 (2H, m, Ar—O—CH₂—CH₂—), 3.48 (2H, t, Br—HC₂—), 4.01 (2H, t, Ar—O—CH₂—), 6.99 (2H, d, Ar—H), 7.36–7.56 (5H, m, Ar—H), 7.75 (4H, q, Ar—H), mp 105–106° C. (temperature at which losing the liquid crystallinity=128–130° C.)

(4) Synthesis of Compound LC-(1)

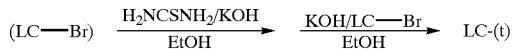

0.4 g of 4-cyano-2'-fluoro terphenyl-4"-dodesiloxyl bromide, 0.09 of thiourea, and 50 ml of deoxygenated ethanol were placed in a flask, stirred, and reflux was implemented under heating. From the point in time where complete dissolving has occurred, reflux is done for 1 day. When the reactants are cooled to room temperature, white crystals are precipitated. This solid material is filtered out, thorough washing in chloroform is performed, and the unreacted bromides are removed. After drying, approximately 0.34 g of a thiourea salt compound was obtained. This salt was thereupon again dissolved under heating in 50 ml of deoxygenated ethanol. A solution of 0.3 g of LC—Br in 50 ml of ethanol was added, stirring was done under heating, and a solution of 50 mg of sodium hydroxide dissolved in 10 ml of distilled water was added dropwise in. After subjecting the reaction mixture to reflux at 80° C. for 6 hours, the temperature was returned to room temperature, and the solid precipitate was filtered out, again washed in ethanol, and dried. After recrystallizing this solid material in chloroform-ethanol, it was purified by silica gel chromatography (chloroform/methanol=32/1). white crystals, constituting the target substance, were obtained (yield=0.14 g).

The results of analyzing the crystals obtained are indicated below.

¹H-NMR (CDCl₃); δ=1.2–1.4 (36H, m, —CH₂—), 1.82 (4H, m, Ar—O—CH₂—CH₂), 2.50 (4H, t, —S—CH₂—), 4.00 (4H, t, Ar—O—CH₂—), 6.99 (4H, d, Ar—H), 7.37–7.55 (10H, m, Ar—H), 7.72 (8H, q, Ar—H), mp 127–128° C. (temperature at which losing the liquid crystallinity=208–209° C.)

(Embodiments 2 and 3) (Synthesis of Compound LC-(2) and Compound LC-(3))

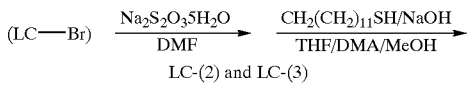

0.6 g of 4-cyano-2'-fluoroterphenyl-4"-dodecyloxy bromide was dissolved in 40 ml of dimethyl formamide (DMF) at 60° C. Into that was slowly added dropwise a solution of 0.3 g of sodium thiosulfate pentahydrate dissolved in 5 ml of water. The mixture was stirred at 65° C. for 4 hours, and then poured into 200 ml of cold water and stirred. A fine colloidal solid of a thiosulfate compound was produced. This was filtered for approximately 1 day. The remaining solid material was suspended in chloroform, the unreacted bromides were removed, filtering was done again, and the solid residue was washed by chloroform-acetone, subsequently it was dried, and a Bunte salt was obtained. Thereupon 0.23 g of 1-dodecane thiol and a mixed solvent of THF and MeOH (12 ml/6 ml), each deaerated, were introduced into the reaction flask and stirred in a nitrogen atmosphere. Thereupon, 0.4 g of sodium hydroxide dissolved in 2 ml of distilled water was added dropwise, and stirring was performed at room temperature for approximately 1 hour. Into this reaction solution was slowly added dropwise 0.45 g of Bunte salt dissolved in a mixed solvent of dimethyl acetoamide (DMA) and MeOH (20 ml/10 ml), under a nitrogen gas flow, and stirring was performed at room temperature for 12 hours. The reaction mixture was then poured into cold water, and the white solid precipitate was filtered out. The filtrate was then washed well in distilled water and acetone, and dried to yield coarse crystals. These coarse crystals were purified by silica gel column chromatography and isolated (chloroform/hexane=4/1). LC-(2) was obtained (yield=0.08 g) as a byproduct in this refining process. The main product obtained from the column was again recrystallized in a mixed solvent of hexane and chloroform to obtain LC-(3) (white crystals) (yield =0.13 g).

The results of analyzing the crystals of the byproduct (LC-(2)) obtained are indicated below.

¹H-NMR (CDCl₃); δ=1.2–1.4 (32H, m, —CH₂—), 1.65 (4H, m, —S—S—CH₂—CH₂), 1.80 (4H, m, Ar—O—CH₂—CH₂—), 2.66 (4H, t, —S—S—CH₂), 3.99 (4H, t, Ar—O—CH₂), 6.97 (4H, d, Ar—H), 7.37–7.55 (10H, m

Ar—H), 7.70 (8H, q, Ar—H); mp 85–87° C. (temperature at which losing the liquid crystallinity=115–117° C.)

The results of analyzing the crystals of main product (LC-(3)) obtained are indicated below.

$^1$H-NMR (CDCl$_3$); δ=0.86 (3H, t, —CH$_3$), 1.2–1.4 (34H, m, —CH$_2$—), 1.65 (4H, m, —S—S—CH$_2$—CH$_2$—), 1.80 (2H, m, Ar—O—CH$_2$—CH$_2$—), 2.66 (4H, t, —S—S—CH$_2$—), 3.99 (2H, t, Ar—O—CH$_2$—), 6.97 (2H, d, Ar—H), 7.37–7.55 (5H, m, Ar—H), 7.70 (4H, q, Ar—H), mp 115–118° C. (temperature at which losing the liquid crystallinity=194–196° C.)

(Test Example 1)

(when an AC voltage was applied)

A gold substrate was immersed in an ethanol solution of the terphenyl skeleton sulfur compound (LC-(3)) of the third embodiment relating to the present invention, and a SAM of the compound LC-(3) was formed on that substrate. The action of this SAM in an electric field was then investigated. In general, it is quite difficult to measure the action of a SAM in an electric field directly. That being so, a method was adopted whereby the dynamic changes produced by the electric field on the SAM formed with the compound LC-(3) relating to the present invention, as described in the foregoing, were observed indirectly, amplifying the motion of the liquid crystals. That observation procedure is described with reference to FIGS. 1 to 4. FIG. 1 is a model diagram representing the condition of a liquid crystal cell containing a SAM formed with the compound LC-(3) (hereinafter called "LC-SAM") with an electric field applied. As diagrammed in FIG. 1, the electrodes of the liquid crystal cell are configured using a gold electrode (50 nm thick) on which the LC-SAM is deployed, and an ITO substrate subjected to a horizontally orienting film process as the opposing electrode, with a cell gap of approximately 5 μm. The liquid crystal material injected inside the cell has such composition that the material has the minimum anisotropic factor of dipolemoment, and the liquid crystals will not move at all in ordinary liquid crystal cells even if electric field is applied thereto. In this cell, when a voltage is applied, the liquid crystals themselves do not move, and so there should be no dynamic change in the liquid crystal phase so long as the LC-SAM portion does not change. Assuming that the LC-SAM has moved in response to the electrodes, the liquid crystal phase will change in response to the motion in the SAM from the liquid crystal molecular phase in immediate contact with the SAM, particularly from the gold electrode interface, out to a thickness of 0.1 μm or so. That movement is communicated successively in the liquid crystal phase. As a result of being propagated and amplified as the motion of the entire liquid crystal(s) present in the 5-micron gap, it becomes possible to observe the minute 2 nm movement resulting from the thickness of the LC-SAM film directly with the naked eye.

Figure 2:
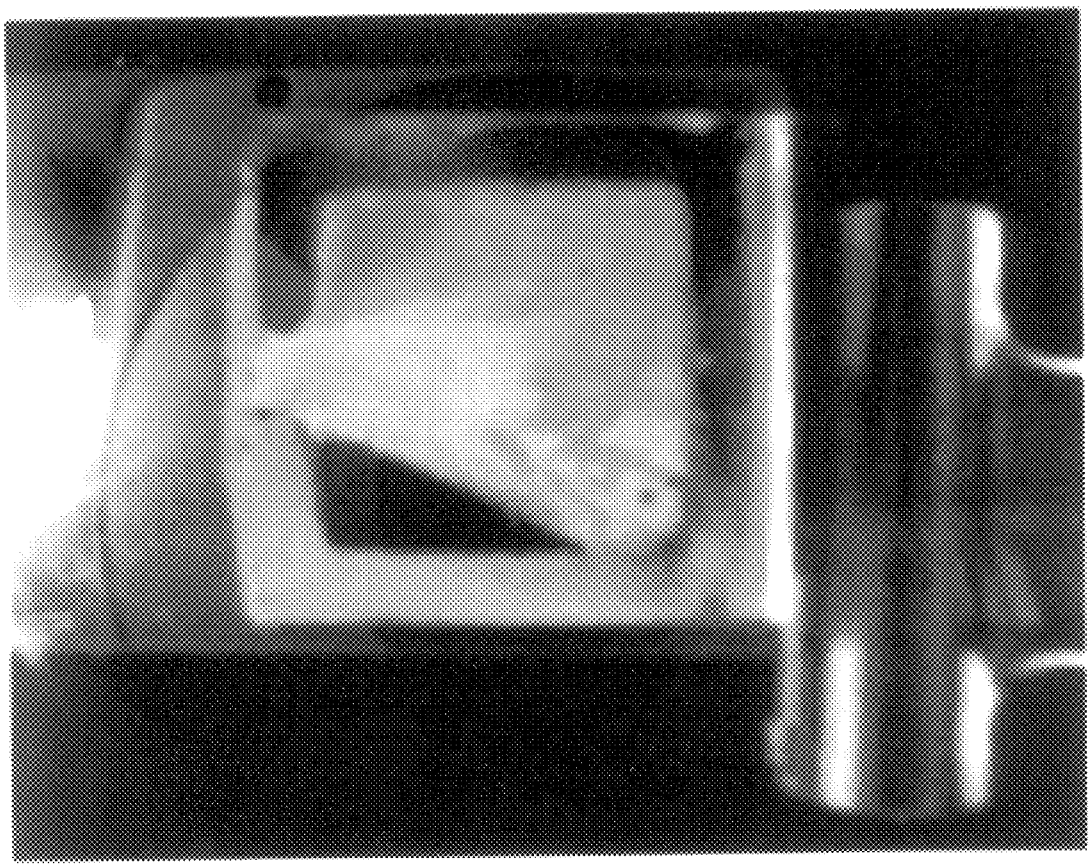
FIG. 2 is a diagram representing light transmissivity in a liquid crystal cell prior to the application of an electric field.
Figure 3:
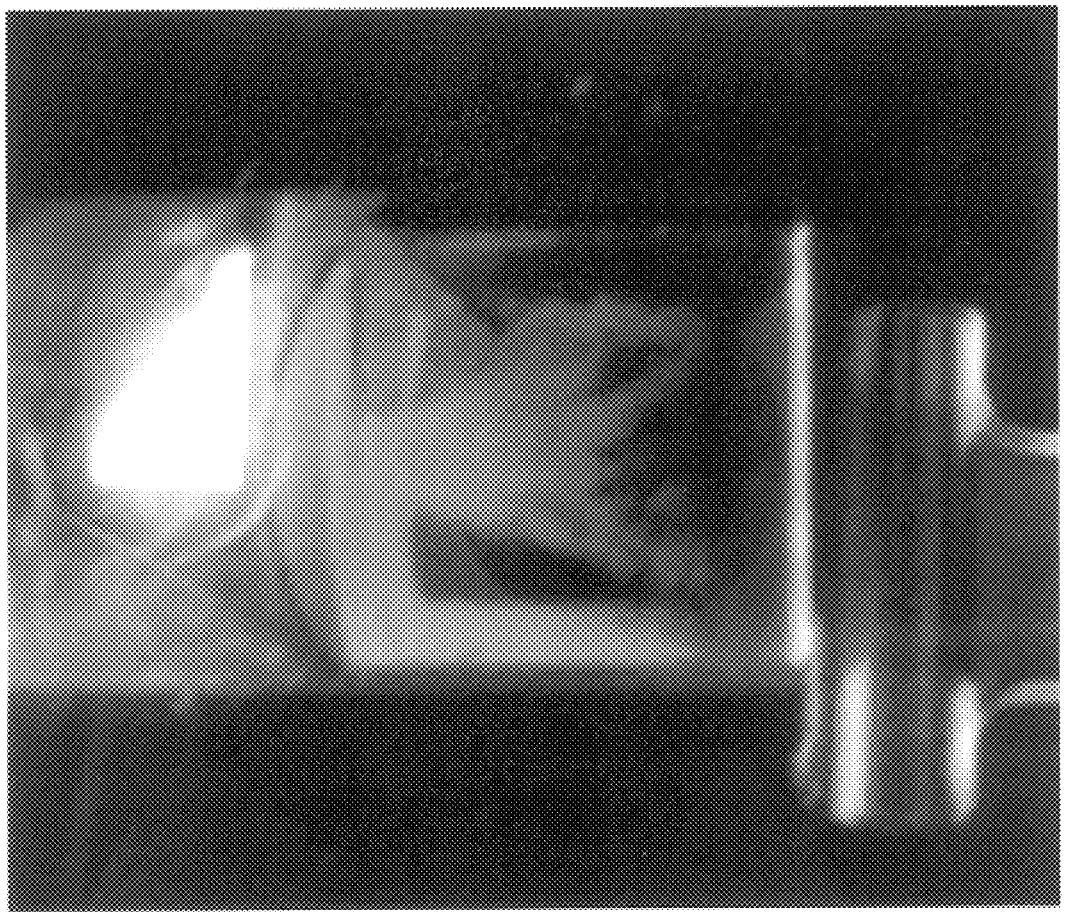
FIG. 3 is a diagram representing light transmissivity in a liquid crystal cell when an AC voltage of 50 V (60 Hz) has been applied.
Figure 4:
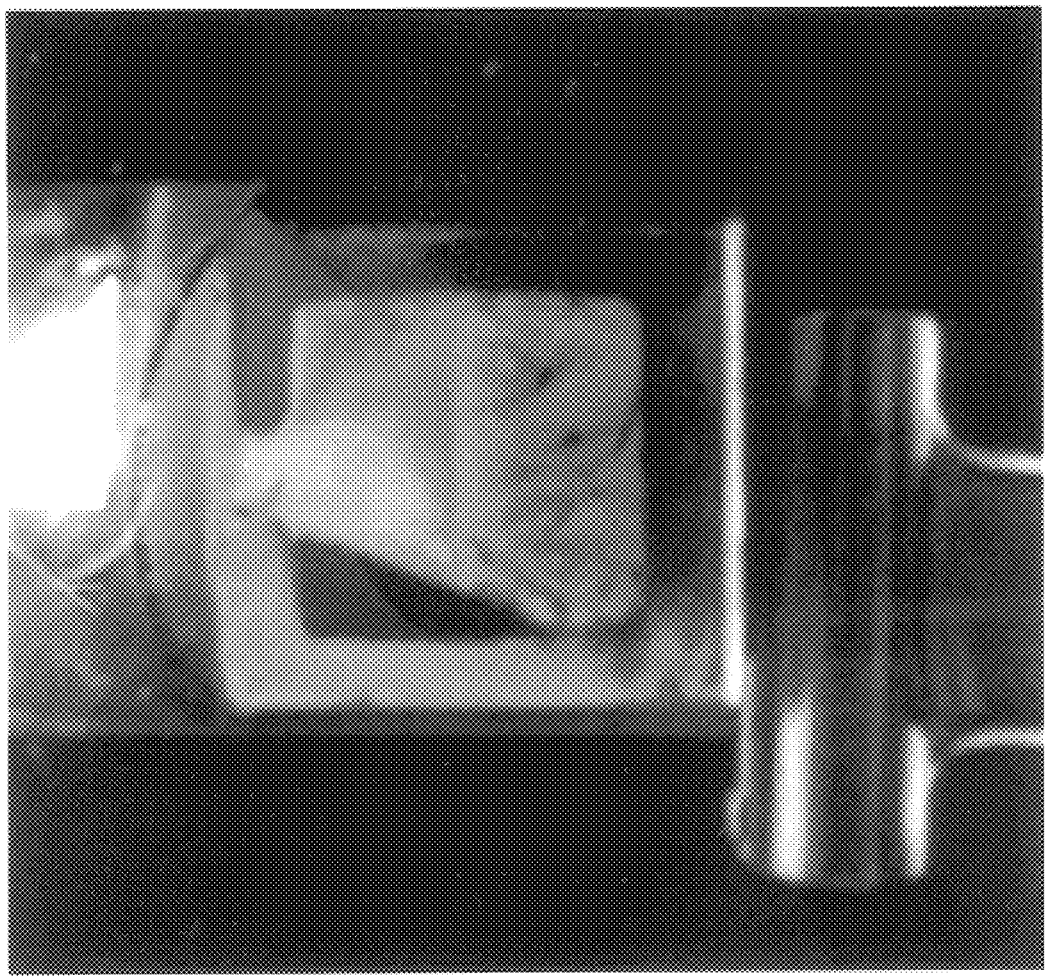
FIG. 4 is a diagram representing light transmissivity in a liquid crystal cell when an electric field has been applied to half of the cell.
Figure 5:
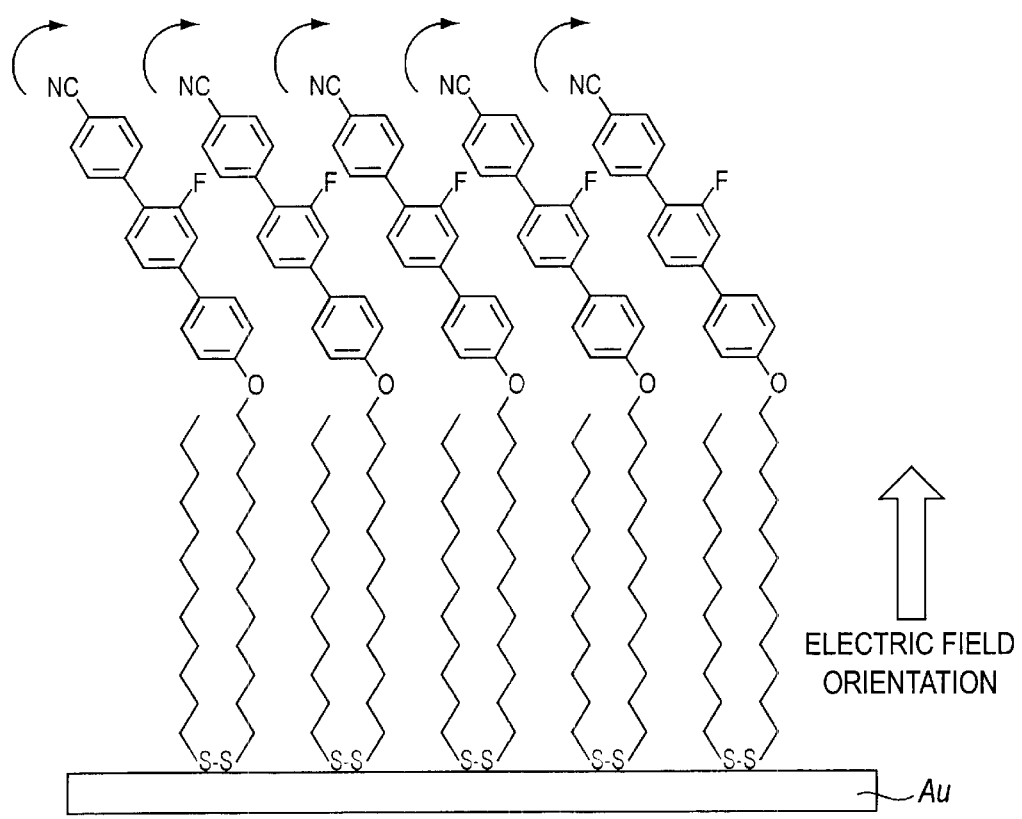
FIG. 5 is a model diagram of a condition of a SAM formed from a terphenyl skeleton sulfur compound relating to the present invention in an electric field.

Using that observation procedure, the dynamic changes in the LC-SAM described in the foregoing in an electric field were observed. A liquid crystal composition was used wherein two types of liquid crystal, namely TL213 and MX961210 made by Merck Corporation, were mixed together in equal proportions. The condition in the liquid crystal cell comprising this liquid crystal composition prior to applying voltage exhibited light transmissivity, as indicated in FIG. 2. When an AC voltage of 50 V (60 Hz) was applied, however, the change in light transmissivity indicated in FIG. 3 was brought about. The condition resulting when a voltage was applied to half of the liquid crystal cell and no voltage was applied to the other half is indicated in FIG. 4. As may be clearly understood from FIG. 4, changes occur in the liquid crystal phase in a liquid crystal cell depending on whether the voltage is turned on or off. When the voltage is turned off, the state indicated in FIG. 2 is returned to, and when the voltage is again applied, the same change is observed to occur, whereupon reversible change induced by a voltage is confirmed. It is also confirmed by measurements of the voltage dependence of the liquid crystal phase only that the liquid crystal does not move with the same voltage, Furthermore, from tests wherein a voltage was applied only to the liquid crystal, no change in motion whatever in the liquid crystal phase was observed in voltage regions where liquid crystal motion is brought about in a liquid crystal cell provided with an LC-SAM. The condition of this LC-SAM in an electric field is believed to be a state such as that indicated in the model diagram in FIG. 5.

Figure 6:
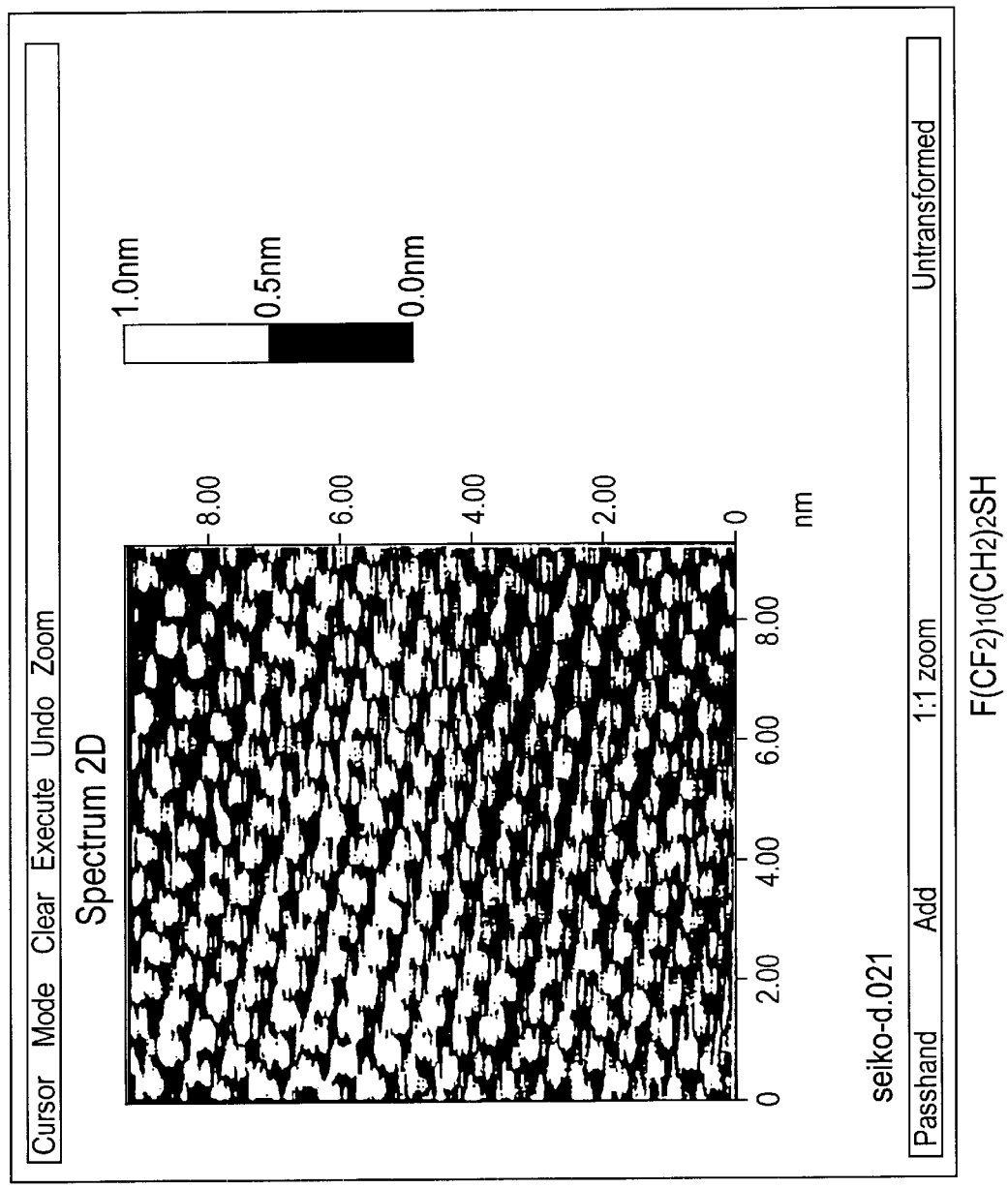
FIG. 6 is an AFM image of a SAM for med from $F(CF_2)_{10}(CH_2)_2SH$ as a comparative compound with no electric field applied.

As to the condition of the LC-SAM when no electric field is applied, it has been confirmed that random conditions appear in an AFM image (not shown). In contrast thereto, the condition under no electric field of a SAM formed as with the compound LC-(3) described above but using F(CF$_2$)$_{10}$(CH$_2$)$_2$SH as a comparative compound was as indicated in FIG. 6, with regularity appearing in the AFM image. It may also be mentioned as an item of information that it is noted in Ishida, T., et al., J. Phys. Chem. B (1999) 103, 1687, that a scanning tunnel microscope (STM) image of a SAM formed from a thiol compound having a terphenyl skeleton like the compound of the present invention appears in a regular condition.

(Test Example 2)

(Liquid crystal surface analysis SPR)

In a liquid crystal cell containing a gold substrate, the gold thin film substrate side was secured tightly onto a prism, and P-polarized light was introduced from the prism. The action of a self-assembled monolayer induced by the application of an electric field was confirmed, using a surface plasmon resonator (SPR) capable of measuring, in real time, dynamic changes at the liquid-surface interface between a self-assembled monolayer provided on the gold surface and the liquid crystal bulk, from the changes in the reflected light selectable on the gold thin film.

Figure 7:
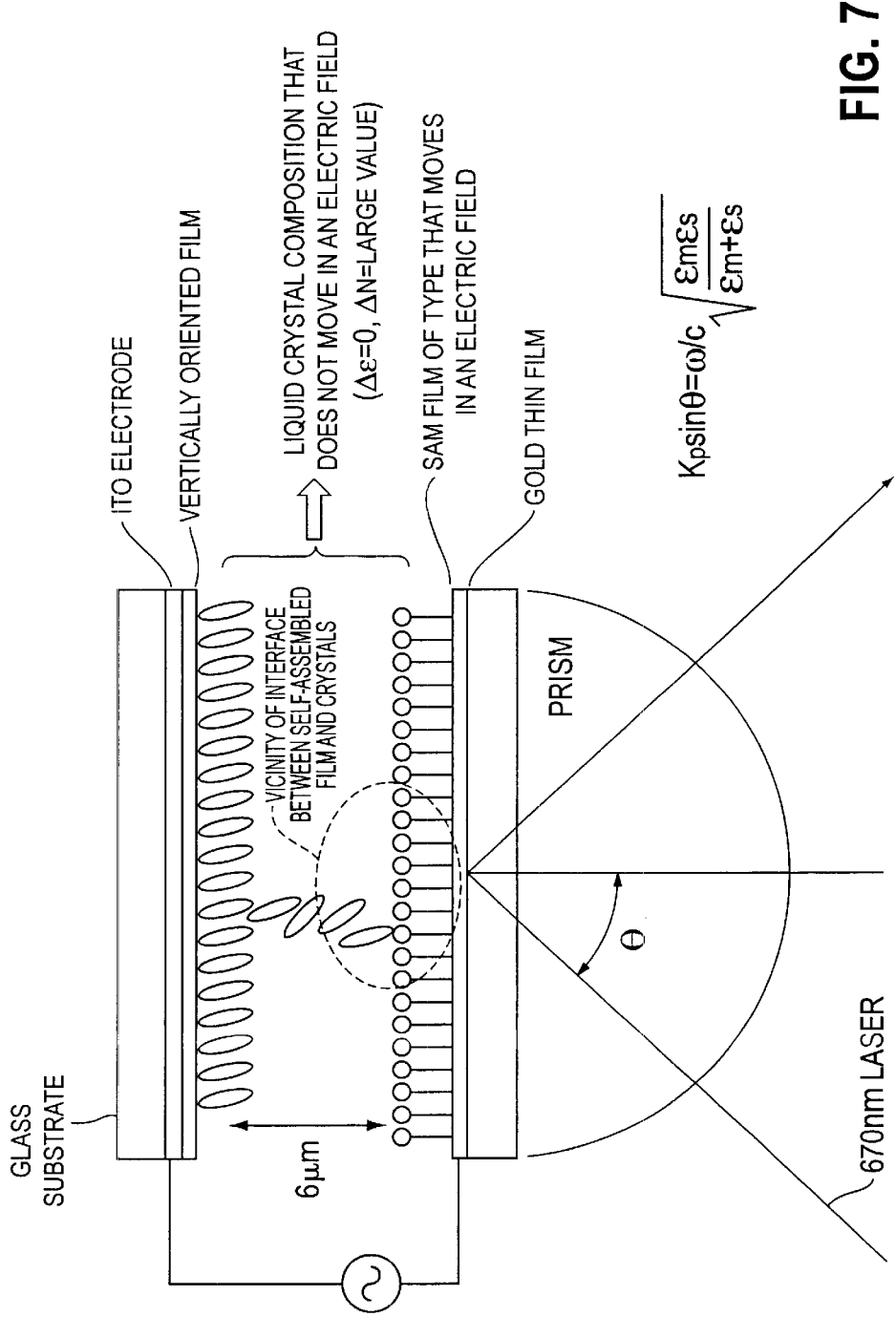
FIG. 7 is a simplified diagram of the basic configuring elements of an SPR measurement system (apparatus) used in test examples.

The basic configuring elements in a specific measurement apparatus are as indicated in the model diagram in FIG. 7. A liquid crystal composition exhibiting very small anisotropic factor of dipolemoment and comparatively large refractive anisotropy, such as a mixture of equal amounts of MX96 1210 and TL213 (made by Merck Corporation), for example, is sealed in a 6-micron gap in the liquid crystal cell. The cell is configured from two different types of electrode surfaces. In one, a self-assembled monolayer containing a thiol is formed on the surface of a gold electrode having a thickness of approximately 500 Ångstroms, while the other is configured with an ITO transparent electrode and a vertically oriented film. The back side of the gold thin film substrate in this liquid crystal cell is made secure to the SPR prism surface. When that is being done, the materials are selected so that the refractive index becomes the same for the substrate and the prism. Materials should be used in the substrate and prism so that the refractive index falls within a range of 1.50 to 2.00, and preferably within a range of 1.70 to 1.85. In this test example, a substrate and prism having a refractive index of 1.73 were used. To further enhance the bonding properties between the substrate and prism, after deploying matching oil having the same refractive index to the prism surface, the liquid crystal cell substrate is made secure to the prism surface. An AC power supply is connected to the liquid crystal cell and an electric field is applied at an AC frequency of 10 Hz in a range of 0 to 15 Vpp. While the electric field is being turned on and off to the liquid crystal cell, the SPR measurement mode is fixed with a time-SPR absorption angle variation plot, and SPR absorption angle change is monitored with the electric field applied at a sampling rate of once every second. A 670 nm semiconductor laser was used for the SPR light source.

The Kp wave number dispersion relationship of the surface plasmon propagated through the interface between the gold thin film and the self-assembled monolayer can be found by solving the equation given below. In this equation, $\varepsilon m$ is the dielectric constant of the self-assembled monolayer, as the dielectric constant of the gold thin film, c the speed of light, and $\theta$ the angle of light incidence.

$$Kp \sin\theta = \omega/c \sqrt{\frac{\varepsilon m \varepsilon s}{\varepsilon m + \varepsilon s}}$$

Figure 8:
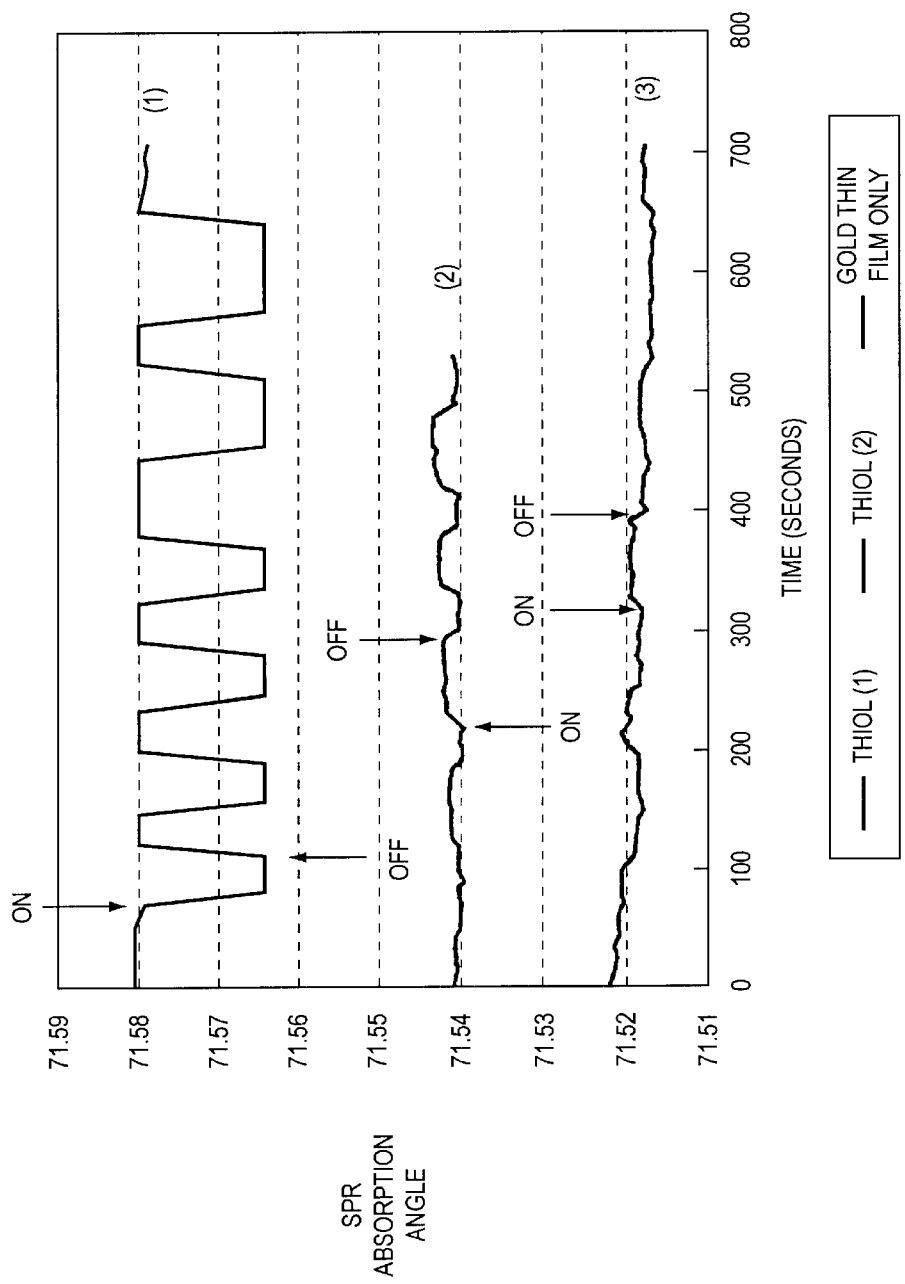
FIG. 8 is a graph representing changes over time in SPR absorption angles in liquid crystal cells.

In this test example, three different gold surface substrates were used in making three different liquid crystal cells, respectively In order to peculiarly modify the surfaces, self-assembled monolayers were formed on the gold thin films, respectively, using a thiol compound (1) (LC-(3) noted earlier) having a liquid crystalline tail group, and, for a comparative test example, using hexadecane thiol (2) having a simple straight-chain methylene structure. With each, a 0.5 mM solution was prepared in dichloromethane, the gold substrates were immersed therein for approximately 1 hour, then washed with dichloromethane and dried under a nitrogen gas flow. In the remaining gold substrate surfaces, liquid crystal cells were fabricated, without making any change or causing anything to adhere. The self-assembled monolayer formed from the liquid crystalline thiol compound (1) becomes like the model diagram represented in FIGS. 5. In FIG. 8 is given a graph wherein the changes in the SPR absorption angle are plotted over time for each liquid crystal cell. With an applied voltage of 7 Vpp, in the liquid crystal cell having compound (1) adhering to the gold surface, the SPR absorption angle declined by about 0.015 with the electric field applied, whereas in the liquid crystal cell having hexadecane thiol (2) adhering, only a very slight change could be verified with the electric field applied. In the liquid crystal cell fabricated with only the gold thin film (3), there was almost no difference between conditions with the electric field similarly applied and not applied, indicating that no dynamic changes are induced in the liquid crystal molecular layer near the gold surface with an electric field applied.

Figure 9:
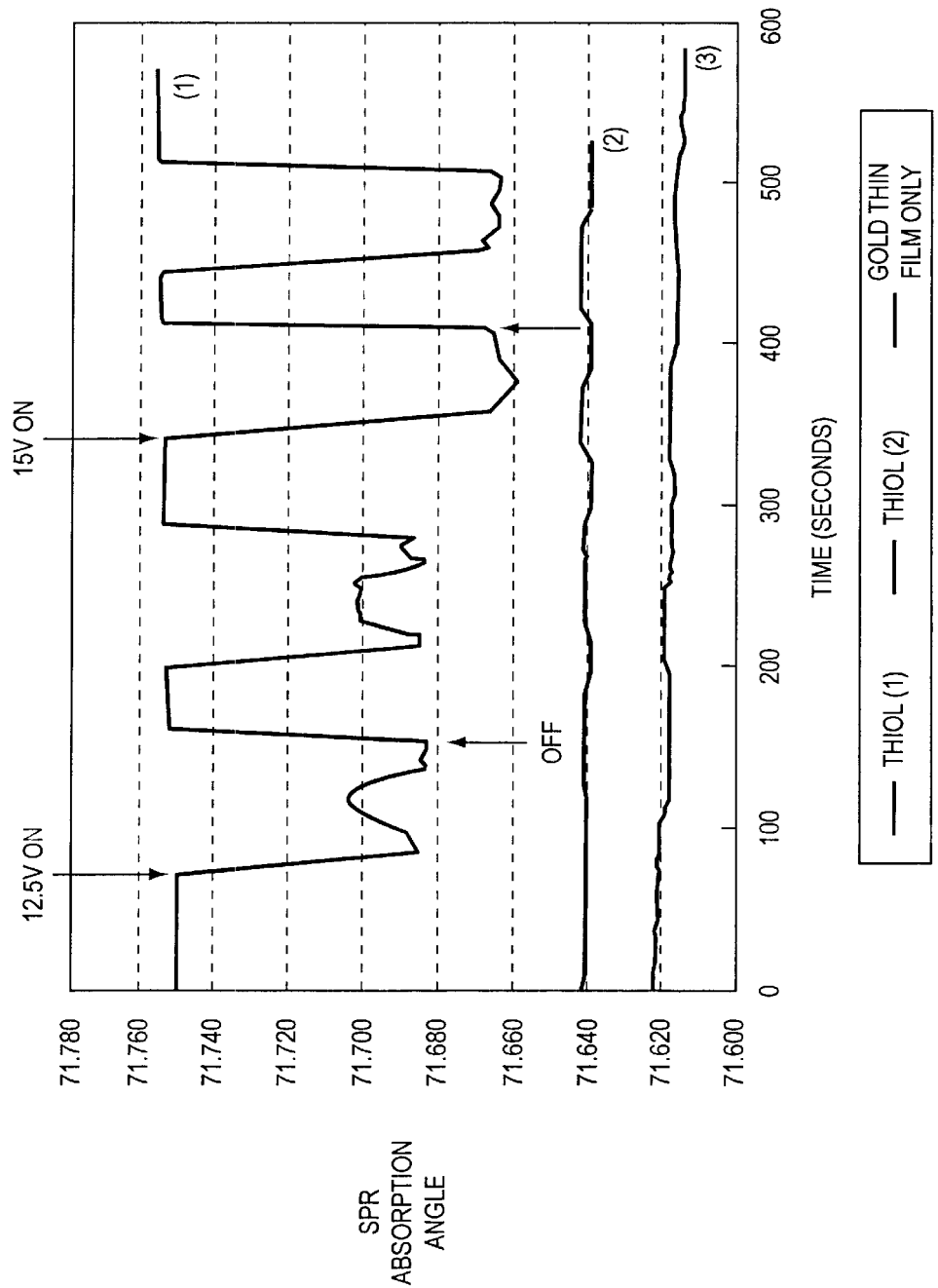
FIG. 9 is a graph representing changes over time in SPR absorption angles in liquid crystal cells.

SPR absorption angle changes were again monitored, with the applied electric field raised further (cf. FIG. 9), but, whereas the compound (1) liquid crystal cell similarly exhibited a large change in the SPR absorption angle, with the hexadecane thiol (2) and gold thin film (3) liquid crystal cells, there was almost no difference when the electric field was turned on and off. Based on these measurement results, these changes were estimated by simulations in order to ascertain the extent of ranges wherein liquid crystal molecules near a gold surface induce dynamic changes due to an electric field, particularly the extents of changes in the thickness direction from the substrate and of changes in the refractive index.

First, the maximum amount of change in the SPR absorption angle observed in a liquid crystal cell containing the compound (1) was approximately 0.09 with an applied voltage of 12.5 Vpp. When the actual change in refractive index is estimated on the basis of that amount of change in the SPR absorption angle, it corresponds to a change of approximately 0.0015, or to approximately 60 Ångstroms in terms of thickness change. In other words, because the thickness of the compound (1) self-assembled monolayer is approximately 30 Ångstroms, it becomes a thickness equivalent to one level of liquid crystal molecules on top of that SAM film (assuming that the liquid crystal molecules are oriented roughly perpendicular to the substrate). Accordingly, it was learned that, in a liquid crystal cell containing a molecular film of this compound (1), under the application of an electric field, no dynamic change is induced in the liquid crystal bulk in the cell, but dynamic change is induced only in the liquid crystal layer at the liquid surface interface containing the molecular film, on the gold thin film. Actually, an investigation was made with an optical microscope to determine whether the liquid crystal bulk in a cell changes with the same electric field, but no visible change could be found at the macro level. Such dynamic changes at the macro level in a self-assembled monolayer, resulting from an electric field, occurring at the substrate interface, could only be observed with the surface plasmon resonance apparatus (SPR) used in this test example. It was also learned, by similar analysis, that dynamic changes are not induced either in the vicinity of the substrate surface or in the liquid crystal bulk, under the application of an electric field, in the liquid crystal cell containing hexadecane thiol and in the liquid crystal cell configured with only a gold thin film.

(Test Example 3)

(Applying a DC voltage)

Figure 10:
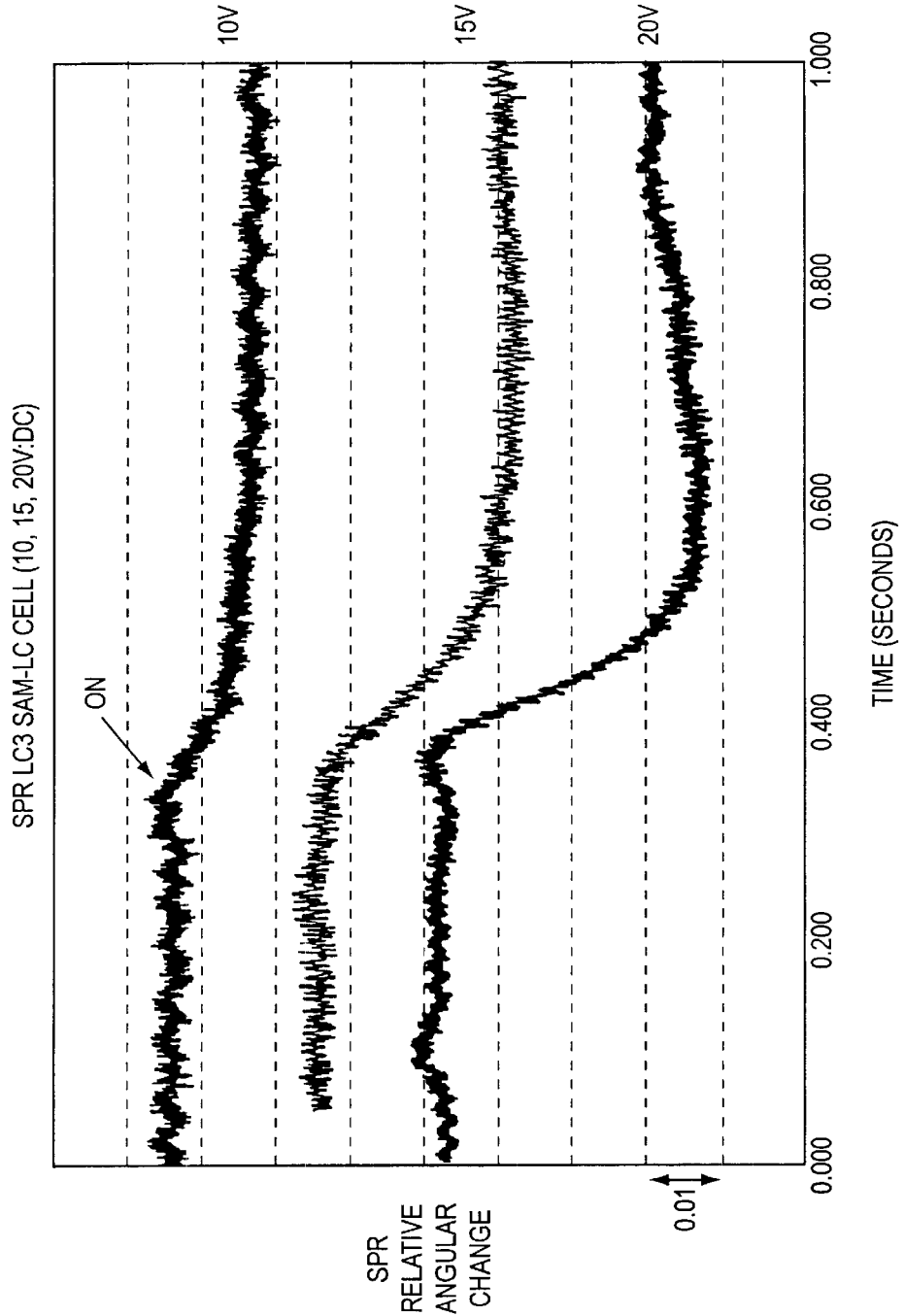
FIG. 10 is a graph representing changes over time in the SPR resonance angle in a liquid crystal cell containing a SAM (LC-SAM) formed from a terphenyl skeleton sulfur compound relating to the present invention under the application of DC voltages of 10 V, 15 V, and 20 V, respectively.
Figure 11:
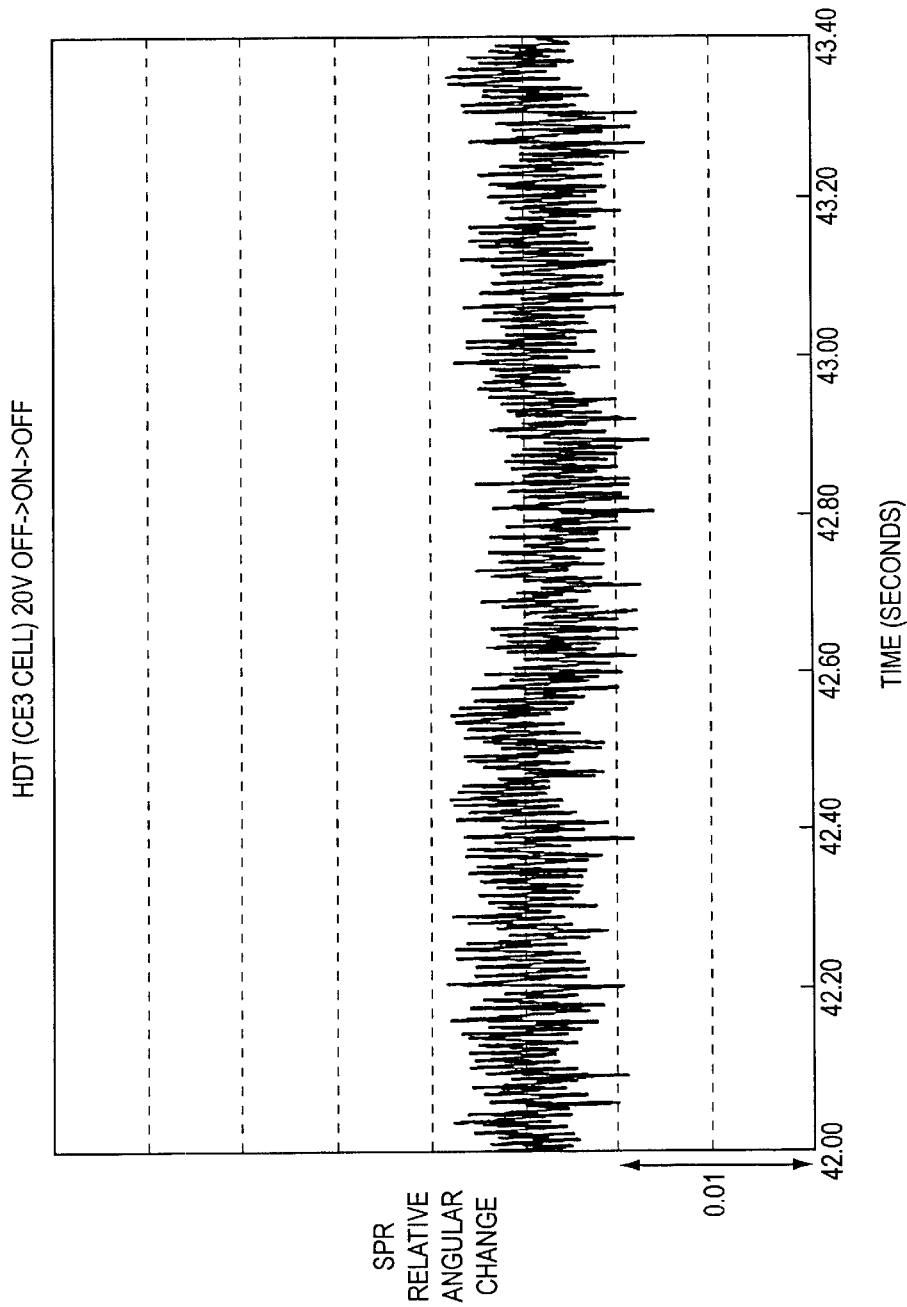
FIG. 11 is a graph representing changes over time in the SPR resonance angle in a liquid crystal cell deployed on an electrode, with hexadecane thiol (HDT) as the molecular film, with a DC voltage (20 V) applied.

When a DC voltage is applied within a range of 10 to 20 V in a liquid crystal cell containing a self-assembled monolayer responsive to an electric field, wherein an LC-SAM is used, surface plasmon resonance (SPR) was observed to occur similarly at various voltages, namely 10 V, 15 V, and 20 V, with the change in SPR resonance angle increasing as the strength of the voltage was increased (cf. FIG. 10). In order to observe changes in the rise in SPR resonance angle when a voltage is applied in real time, moreover, changes induced in the SPR resonance angle by voltages were observed in a high-speed mode where the measurement sampling frequency was 1 sampling/0.1 ms. As a result, it was determined that a time of approximately 100 to 150 ms is required from the application of the voltage until the SPR resonance angle change rises and becomes saturated. In these measurements, as with the AC application tests in test example 1, the anisotropic factor of dipolemoment of the liquid crystal composition is close to (equal to) zero. Accordingly, it is only the self-assembled monolayer immobilised on the electrode surface that responds when an electric field is applied, and the time-sequence changes in the SPR resonance angle can be explained as resulting from the capture of dynamic changes in the electric field-responsive molecular film. In the case of a liquid crystal cell deployed on an electrode having an alkane thiol (hexadecane thiol; HDT) not response to an electric field as the molecular film, on the other hand, no change in the SPR resonance angle was observed to occur with the same DC voltage applied (cf. FIG. 11).

Based on the present invention, a new terphenyl skeleton sulfur compound is provided. The terphenyl skeleton sulfur compound of the present invention exhibits high anisotropic factor of dipolemoment and liquid crystal properties.

Based on the present invention, moreover, a synthetic method for the new terphenyl skeleton sulfur compound noted above is provided.

Based on the present invention, furthermore, a self-assembled monolayer (wherein the new terphenyl skeleton sulfur compound noted above is used) is provided. This self-assembled monolayer is a new functional thin film therewith, by the application of an electric field or other external stimulus, the molecules and molecular aggregates configuring the self-assembled monolayer can be dynamically changed, and the surface properties of the entire film surface can be reversibly controlled.

What is claimed is:

1. A terphenyl skeleton sulfur compound represented by formula (I) below.

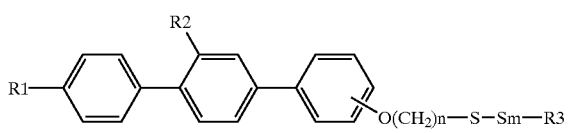

(I)

where R1 is a nitrile group, halogen atom, hydrogen atom, methyl group, or trifluoromethyl group, R2 is a halogen atom, nitrile group, or trifluoromethyl group, R3 is

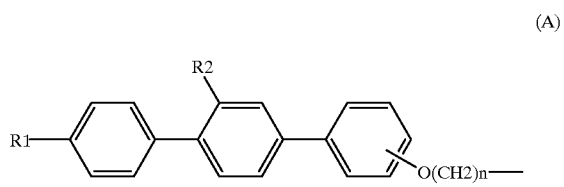

(A)

or an alkyl group having 1 to 20 carbon atoms, n is a number from 1 to 20, and m is 0 or 1.

2. The terphenyl skeleton sulfur compound according to claim 1 wherein n in said general formula (I) is 5 to 18.

3. The terphenyl skeleton sulfur compound according to claim 1 wherein n in said formula (I) is 8 to 14.

4. A method for manufacturing, producing or forming any one of terphenyl skeleton sulfur compounds according to claim 1, comprising: obtaining a methoxy terphenyl derivative from a bromobiphenyl derivative and methoxybenzene boric acid; obtaining a hydroxy terphenyl derivative from the methoxy terphenyl derivative and tribromoborane; obtaining a terphenyl alkyloxy bromide derivative from the hydroxy terphenyl derivative and a dibromo alkane; and causing the bromide derivative and thiourea to react, or, alternatively, causing the bromide derivative, sodium thiosulfate pentahydrate, and an alkane thiol to react.

5. A self-assembled monolayer comprises a terphenyl skeleton sulfur compound according to claim 1.

6. A method for manufacturing, producing or forming any one of terphenyl skeleton sulfur compounds according to claim 2, comprising: obtaining a methoxy terphenyl derivative from a bromobiphenyl derivative and methoxybenzene boric acid; obtaining a hydroxy terphenyl derivative from the methoxy terphenyl derivative and tribromoborane; obtaining a terphenyl alkyloxy bromide derivative from the hydroxy terphenyl derivative and a dibromo alkane; and causing the bromide derivative and thiourea to react, or, alternately, causing the bromide derivative, sodium thiosulfate pentahydrate, and an alkane thiol to react.

7. A method for manufacturing, producing or forming any one of terphenyl skeleton sulfur compounds according to claim 3, comprising: obtaining a methoxy terphenyl derivative from a bromobiphenyl derivative and methoxybenzene boric acid; obtaining a hydroxy terphenyl derivative from the methoxy terphenyl derivative and tribromoborane; obtaining a terphenyl alkyloxy bromide derivative from the hydroxy terphenyl derivative and a dibromo alkane; and causing the bromide derivative and thiourea to react, or, alternatively, causing the bromide derivative, sodium thiosulfate pentahydrate, and an alkane thiol to react.

8. A self-assembled monolayer comprising a terphenyl skeleton sulfur compound according to claim 2.

9. A self-assembled monolayer comprising a terphenyl skeleton sulfur compound according to claim 3.

* * * * *